(12) United States Patent
Beilfuss et al.

(10) Patent No.: US 7,537,776 B1
(45) Date of Patent: May 26, 2009

(54) LIQUID CONCENTRATE FOR PRESERVING COSMETICS

(75) Inventors: Wolfgang Beilfuss, Hamburg (DE); Gisela Hahn, Alveslohe (DE); Klaus Weber, Hamburg (DE); Ralf Gradke, Tornesch (DE)

(73) Assignee: Air Liquide Sante (International), Paris Cedex (FR)

( * ) Notice: Subject to any disclaimer, the term of this patent is extended or adjusted under 35 U.S.C. 154(b) by 0 days.

(21) Appl. No.: 09/959,931

(22) PCT Filed: Mar. 27, 2000

(86) PCT No.: PCT/IB00/00352

§ 371 (c)(1),
(2), (4) Date: Nov. 13, 2001

(87) PCT Pub. No.: WO00/67705

PCT Pub. Date: Nov. 16, 2000

(30) Foreign Application Priority Data

May 10, 1999  (DE)  .................................. 199 22 538

(51) Int. Cl.
*A01N 25/00* (2006.01)
*A61K 8/02* (2006.01)
(52) U.S. Cl. .................. 424/405; 424/401; 424/70.1
(58) Field of Classification Search ................. 424/405, 424/401, 70.1
See application file for complete search history.

(56) References Cited

U.S. PATENT DOCUMENTS

| | | | | |
|---|---|---|---|---|
| 5,100,656 A | * | 3/1992 | Lang et al. | ............... 424/70.19 |
| 5,332,765 A | * | 7/1994 | Lorentzen et al. | ............ 523/122 |
| 5,490,955 A | * | 2/1996 | Hagan et al. | ................. 510/127 |
| 5,670,160 A | * | 9/1997 | Eggensperger et al. | ...... 424/405 |
| 5,733,362 A | * | 3/1998 | Hahn | ...................... 106/18.33 |
| 5,968,539 A | * | 10/1999 | Beerse et al. | ................ 424/405 |
| 6,120,656 A | * | 9/2000 | Okano | .................... 204/192.12 |
| 6,120,758 A | * | 9/2000 | Siddiqui et al. | .......... 424/78.02 |
| 6,294,186 B1 | * | 9/2001 | Beerse et al. | ................ 424/405 |

FOREIGN PATENT DOCUMENTS

| | | |
|---|---|---|
| DE | 40 26 756 | 2/1992 |
| EP | 0 252 256 | 1/1988 |
| EP | 0 521 651 | 1/1993 |
| EP | 0 570 794 | 11/1993 |
| WO | 93/19149 | 9/1993 |
| WO | WO 96/00060 | 1/1996 |
| WO | 96/20993 | 7/1996 |

OTHER PUBLICATIONS

Hawley, The Condensed Chemical Dictionary, 10th Ed., Van Nostrand Reinhold Co., New York, (1981), pp. 121, 434, 854 and 933.*
Flick, E., Cosmetic and Toiletry Formulations, 1999, 2nd Ed., vol. 7, Noyes Publications William Andrew Publishing, 1999, pp. 74 and 273.*
Flick, E., Cosmetics Additives, 1991, Noyes Publications, p. 646.*

* cited by examiner

*Primary Examiner*—Gina C. Yu
(74) *Attorney, Agent, or Firm*—Young & Thompson

(57) ABSTRACT

A liquid concentrate for preserving cosmetic products includes a combination of carboxylic acid salts chosen from the salts of benzoic acid, propionic acid, salicylic acid, sorbic acid, 4-hydroxybenzoic acid, dehydracetic acid, formic acid or 10-undecylenic acid and alcohols chosen from 2-phenozyethanol, benzyl alcohol, phenethyl alcohol, 1-phenoxypropan-2-ol, 3-(4-chlorophenoxy)-1,2-propanediol, chlorobutanol or 2,4-dichlorobenzyl alcohol in a solvent, where the active ingredient content is greater than 45% by weight.

15 Claims, No Drawings

LIQUID CONCENTRATE FOR PRESERVING COSMETICS

The invention relates to a liquid concentrate based on carboxylic acid salts and alcohols, and to its use for preserving cosmetic products.

Cosmetic products, in particular "rinse-off" products such as shampoos, the pH of which does not usually exceed 5-6, are being increasingly preserved using organic acids or salts thereof in combination with alcohols since acids and alcohols alone are inadequate for preserving cosmetics. These substances are frequently individually matched to the products and used on their own. Also known is the use of active ingredient combinations in use concentrations.

DE-A-40 26 756 discloses a preservative for "rinse-off" products which is formed from carboxylic acid or salts thereof, alcohol and polyhexamethylene biguanide salts. Each of these three components is essential for the achieved effect. The use of biguanide salts in anionic-surfactant-based "rinse-off" products such as shampoos is problematical since it can result in interaction with the formation of precipitates and/or inactivation of the action.

The known preservatives also have the disadvantage that they are insufficiently stable, in particular at low temperatures, when the content of active ingredients is high.

The object of the invention was therefore to provide a liquid concentrate with a high active ingredient content and based on an active ingredient combination of carboxylic acid salts and alcohols and containing as little as possible auxiliary (solvent), which has high microbiological and physical (including low-temperature) stability and additionally offers handling and cost advantages over known preservatives.

To achieve this object, a liquid concentrate is proposed in accordance with Claim 1 which consists of a carboxylic acid component (A), an alcohol component (B), a solvent (C) and optionally other auxiliaries, additives and/or active ingredients, the carboxylic acid component (A) comprising at least one salt chosen from the salts of benzoic acid, propionic acid, salicylic acid, sorbic acid, 4-hydroxybenzoic acid, dehydracetic acid, formic acid or 10-undecylenic acid and optionally also one or more of said free acids, and the alcohol component (B) comprising at least one alcohol chosen from 2-phenoxyethanol, benzyl alcohol, phenethyl alcohol, 1-phenoxypropan-2-ol, 3-(4-chlorophenoxy)-1,2-propanediol, chlorobutanol or 2,4-dichlorobenzyl alcohol, the total content. of components A and B, based on the total concentrate, being greater than 45% by weight and the liquid concentrate not comprising polyhexamethylene biguanide salt.

The carboxylic acid component (A) preferably comprises benzoic acid salts and/or sorbic acid salts, Na benzoate and K sorbate being most preferred. The alcohol component (B) preferably comprises 2-phenoxyethanol, benzyl alcohol and/or 1-phenoxypropan-2-ol, 2-phenoxyethanol and benzyl alcohol being most preferred.

A large number of substances or combinations of substances can be used as further additives, auxiliaries or active ingredients (cosmetic additives) for the base formulation (instead of the acids given below, the corresponding salts are optionally used). The additives can be anionic or cationic, the presence of polyhexamethylene biguanide salts, however, being excluded. Examples of additives are skincare substances and moisturizing agents (e.g. glycolic acid, lactic acid, urea, arginine), complexing agents (e.g. EDTA), antimicrobial active ingredients (e.g. triclosan, o-phenylphenol, Tinosan HP 100), essential oils and natural extracts (e.g. tea tree oil, green tea, hinokitiol and geraniol), amphoteric surfactants, surfactants, cleansing additives and disinfection active ingredients (e.g. cocoamidopropylbetaine), perfumes, antiacne and antidandruff active ingredients (e.g. Octopirox, Lipacide C8G and zinc pyrithione), fungicides (e.g. clotrimazole), dyes, corrosion inhibitors (e.g. benzotriazole), disinfection active ingredients and antiseptics (e.g. chlorohexidine salts and octenidine dihydrochloride), bitter substances (e.g. denatonium salts), sunscreens (e.g. 2-phenylbenzimidazole-sulphonic acid), deodorant active ingredients (e.g. zinc phenolsulphonate), oral hygiene active ingredients (e.g. potassium monofluorophosphate), preservatives (e.g. hydroxymethylglycine, diazolidinylurea, imidazolidinylurea, N-methylisothiazolone, 5-chloro-2-methylisothiazolone, bronopol, bronidox, triclocarban, 4-chloro-m-cresol, 4-chloro-3,5-dimethylphenol, thymol and dibromodicyanobutane), formaldehyde donor compounds, isothiazolones, phenols, carbohydrate compounds (such as alkyl polyglycosides, starch and cellulose derivatives and cyclodextrins), alkali metal chlorides (e.g. NaCl or KCl), anionic surfactants (such as lauryl ether sulphates), plant extracts and oils. Possible cationic active ingredients, such as chlorhexidine salts and quaternary ammonium salts (e.g. benzalkonium chloride, cetyl trimethylammonium chloride or bromide, cetylpyridinium chloride, benzethonium chloride and didecyldimethylammonium chloride), can be used.

Many of these cosmetics additives have a multifunctional action. In addition, synergistic increases in action of the liquid concentrates according to the invention containing the additives can sometimes arise. In this connection, combinations of purely naturally occurring or nature-identical active ingredients are preferred, a preferred embodiment accordingly comprising benzoic acid or its salts and/or sorbic acid or its salts and/or benzyl alcohol and/or phenethyl alcohol, optionally water and optionally essential oils.

The active ingredients of the liquid concentrates according to the invention belong to the so-called soft preservative active ingredients, i.e. they are sufficiently effective at a relatively high use concentration. To improve the effectiveness and/or to broaden the activity spectrum, they can, if required, also be combined with other more effective active ingredients, e.g. preserving additives, e.g. formaldehyde donor compounds, such as DMDMH, diazolidinylurea, imidazolidinylurea, hydroxymethylglycine salts and IPBC.

In an alternative preferred embodiment, cationic additives are excluded.

The concentrates according to the invention are further suitable as additive having microbicidal and disinfecting properties in washing and cleaning formulations. As well as preserving the mostly water-based end products, the concentrates according to the invention contribute to the antimicrobial effectiveness of the cleaning, care and hygiene products for the home (e.g. antimicrobial hand cleansers) and bodycare (e.g. toothpastes).

In the individual case, the type and amount of other active ingredients can be established by the person skilled in the art in a simple and rapid manner by a few experiments, where the resulting active ingredient system, which comprises the liquid concentrate according to the invention, can have a broad or else a very specific use potential.

The preferred solvent is water.

Preference is given to preparing liquid concentrates with a high active ingredient content and a relatively low solvent content. For example, the total content of the carboxylic acid component and of the alcohol component is 60% or greater and in particular is 80% or greater, and the solvent content is 40% or lower or 20% or lower.

The high active ingredient content of the liquid concentrate according to the invention is surprisingly achieved using carboxylic acid salts, as opposed to the pure, free acids, in combination with the alcohols. Attempts to achieve the high degrees of concentration according to the invention only using free acids while also formulating a stable concentrate have failed.

The concentrates are prepared by simple mixing. For example, the salts are dissolved in water with stirring, and the alcohols are stirred in to give a homogeneous mixture.

It is advantageous if the liquid concentrates according to the invention can, because of their solubility in water, be incorporated into the cosmetic products by simple dilution. This offers handling and cost advantages over the use of individual substances, which may be powders or granules (e.g. Na benzoate or K sorbate) or liquids (e.g. phenoxyethanol). As a result of the high active ingredient content in the concentrate (preferably greater than 80%), it is also possible to reduce storage and transport costs.

An addition of the alcohols according to the invention appears to reduce crystallization of the acid salts in the preparation, in particular upon evaporation (e.g. at the pack opening) or upon supercooling. Accordingly, it is likely that the low-temperature stability of the liquid concentrate is also improved, in particular during transportation or storage at low temperatures. Even at, for example, −5° C., the concentrate remains surprisingly liquid and pumpable.

In this connection, it is not mandatory that the liquid concentrate according to the invention arises as a clear solution, it is also possible to use homogeneous-disperse preparations. However, the homogeneous-disperse preparation is preferably free from relatively large amounts of active ingredients which have crystallized out.

In addition, the alcohols also serve as preservative for the weakly alkaline, water-based salt concentrates, which have an insufficient antimicrobial activity on their own in this pH range. Without the addition of alcohol undesired microbial growth occurs in border areas in the preparation (e.g. due to dilution effects as a result of the formation of condensation or upon dilution with water).

Furthermore, the alcohols according to the invention have an adequate and desirable antimicrobial vapour phase action, which contributes to ensuring preservation of the "rinse-off" products. As a result, a broad spectrum of activity is achieved.

Since the concentrates according to the invention are also suitable as solvents or solubilizers or carriers for other active ingredients, it is possible to minimize or exclude completely the use of otherwise customary solvents without antimicrobial activity.

The concentrates are stable over a broad pH range. Any precipitates at a low pH dissolve upon dilution or are reversible by pH correction.

The liquid concentrates according to the invention have a low residual risk upon use and are sufficiently safe.

If desired, the liquid concentrates according to the invention can be formulated such that in some circumstances they have a particular colour stability (see Example 5). Thus, it has surprisingly been found that the colour stability can be increased by the use of K salts or optionally substituted ammonium salts instead of Na salts, in particular exchange of Na benzoate for K benzoate, and/or the use of specific additives, such as citric acid and salts thereof, mandelic acid and salts thereof, DMDMH (dimethyldimethylolhydantoin), BHT (e.g. 2,6-di-tert-butyl-p-cresol), BHA (3-tert-butyl-4-hydroxyanisole), Sensiva SC 50 (1-(2-ethylhexyl)glyceryl ether or 3-((2-ethylhexyl)oxy)-1,2-propanediol), ascorbic acid or salts or compounds thereof, such as 6-O-palmitoyl-L-ascorbic acid, vitamin E or synthetic and/or natural derivatives thereof, gallic acid and salts and derivatives thereof. Preferred colour-stabilizing additives are alkali metal citrates, alkali metal mandelates, DMDMH and vitamin E, particular preference being given to the addition of vitamin E for improving the colour stability.

In particular, the concentrates according to the invention thus have the following advantages:

liquid;

high active ingredient content, low solvent content;

handling and cost advantages;

broad spectrum of activity, including vapour phase activity;

water-based, comprise (preferably) only active ingredients and water as solvent;

stable over broad pH and temperature ranges;

soluble in water (in the end product and in predilutions);

can be used as solvent, solubilizer or carrier for other ingredients (e.g. perfume or the like) in the production of cosmetics;

safe—low residual risk upon use;

stable at low temperatures, liquid and pumpable at low temperatures;

miscible, compatible with an extensive range of ingredients, and good colour stability, even upon prolonged storage and/or at elevated temperatures.

The concentrates according to the invention are suitable for the preparation of cosmetic products, in particular for "rinse-off" products such as shampoos, the pH of which is usually less than 7, in particular less than 6.

The invention is illustrated in more detail by reference to the following examples. Unless stated otherwise, all percentages are by weight.

The Hazen colour number is the number of mg of platinum [as potassium hexachloroplatinate(IV) containing cobalt(II) chloride hexahydrate in a ratio of 1.246:1 dissolved in 1000 ml of aqueous hydrochloric acid] which has virtually the same colour as the sample when the path length is the same.

EXAMPLE 1

Preparation and Properties of Liquid Concentrates Based on Na Benzoate, K Sorbate and Phenoxyethanol Liquid concentrates having the following composition were prepared:

TABLE 1

| Presolution - constituents | % (w/w) | Initial weight in g |
|---|---|---|
| Na benzoate | 30.00 | 1440.0 |
| Sorbic acid | 11.20 | 537.6 |
| Potassium hydroxide solution (45%) | 12.25 | 588.0 |
| Demin. Water | 43.55 | 2090.4 |
| | 97.0 | 4656.0 |

(Data refers to the weight of the finished formulations)

2090.4 9 of demineralized (demin.) water were introduced initially and 588.0 g of potassium hydroxide solution were added with stirring. The mixture was then placed in an ice bath, and the 537.6 g of sorbic acid were slowly added, as a result of which the temperature rose only very slightly. Then, likewise with stirring, the 1440.0 g of Na benzoate were added, and the mixture was stirred for a prolonged period. The solution was filtered and was clear and yellowish (colour number Hazen 46; Gardner 0.1).

Then, 970 g of the presolution were weighed out three times and 5, 10 and 15 g of phenoxyethanol were added. The amount in each case was divided into thirds and adjusted to the various pH values using a few drops of 45% and 5% strength potassium hydroxide solution. For samples without phenoxyethanol, 323.33 g of presolution were weighed out and then likewise adjusted to the various pH values. Each of these samples was then made up to 333.33 g with demin. water.

This resulted in the preparation of the following formulations:

TABLE 2

| Formulation | A(%) | B(%) | C(%) | D(%) | E(%) | F(%) |
|---|---|---|---|---|---|---|
| Na benzoate | 30.00 | 30.00 | 30.00 | 30.00 | 30.00 | 30.00 |
| Sorbic acid | 11.20 | 11.20 | 11.20 | 11.20 | 11.20 | 11.20 |
| Potassium hydroxide solution (45%) | 12.25 | 12.25 | 12.25 | 12.25 | 12.25 | 12.25 |
| Demin. water | 46.05 | 46.05 | 46.05 | 45.55 | 45.55 | 45.55 |
| Phenoxyethanol | 0.05 | 0.50 | 0.05 | 1.00 | 1.00 | 1.00 |
| pH | 8.60 | 9.25 | 10.02 | 8.60 | 9.25 | 10.02 |

| Formulation | G(%) | H(%) | I(%) | J(%) | K(%) | L(%) |
|---|---|---|---|---|---|---|
| Na benzoate | 30.00 | 30.00 | 30.00 | 30.00 | 30.00 | 30.00 |
| Sorbic acid | 11.20 | 11.20 | 11.20 | 11.20 | 11.20 | 11.20 |
| Potassium hydroxide solution (45%) | 12.25 | 12.25 | 12.25 | 12.25 | 12.25 | 12.25 |
| Demin. Water | 45.05 | 45.05 | 45.05 | 46.55 | 46.55 | 46.55 |
| Phenoxyethanol | 1.05 | 1.50 | 1.05 | | | |
| pH | 8.60 | 9.25 | 10.02 | 8.60 | 9.25 | 10.02 |

(Data in % by weight)

The formulations A-L were then tested for physical stability and microbiological activity and stability.

1. Physical Stability

The solutions are still as clear after 3 months at −5° C. This shows that the liquid concentrates have high physical stability.

2. Microbiological Stability and Activity

Formulations A-L and their 50% strength aqueous solutions were examined using the method described in Example 4 for their effectiveness as preservatives against various microbes.

It has been found that without the addition of phenoxyethanol the formulations and their 50% strength aqueous solutions are not sufficiently microbiologically stable. The phenoxyethanol-free solutions have a certain susceptibility to microbial growth, depending on the pH and the degree of dilution. Thus, for example, the formulation K, in 50% strength dilution in demineralized water (pH of the dilute formulation 9.28) fails the test described in Example 4 after storage for about 2 weeks (moderate growth), and the 50% strength dilution of formulation L (pH of the dilute formulation 10.02) fails this test after storage for just approximately one week (moderate growth).

Preservation of these preparations is therefore necessary by, for example as according to the present invention, adding phenoxyethanol.

EXAMPLE 2

Preparation of Liquid Concentrates Based on K Sorbate or Sorbic Acid, Benzyl Alcohol and Phenoxyethanol Liquid concentrates having the following composition were prepared:

TABLE 3

| Formulation | M (parts/%) | N (parts/%) |
|---|---|---|
| K sorbate | 5/38.5% | |
| Benzyl alcohol | 5/38.5% | 5/38.5% |
| Phenoxyethanol | 3/23% | 3/23% |
| Sorbic acid | | 5/38.5% |
| Appearance after stirring for 24 h at room temperature | no clear solution/ thick white residue | no clear solution/ thick white residue |

| Formulation | O (parts/%) | P (parts/%) | R (parts/%) |
|---|---|---|---|
| K sorbate | 3/23% | | |
| Benzyl alcohol | 5/38.5% | 5/40.85% | 5/20% |
| Phenoxyethanol | 5/38.5% | 5/40.85% | 5/20% |
| Sorbic acid | | 2.24/18.30% | 2.24/8.96% |
| 1-Methoxypropan-2-ol | | | 12.76/51.04% |
| Appearance after stirring for 24 h at room temperature | no clear solution | no clear solution | clear colourless solution |

It is clear from Table 3 that it is not possible to obtain a homogeneous, stable concentrate (formulations M to P) using K sorbate or using sorbic acid. Only the use of considerable amounts of an organic solvent leads to a liquid concentrate (formulation R). The low-temperature stability of this liquid concentrate (R) is not, however, adequate: After storage at −5° C., some of the sorbic acid crystallizes out.

EXAMPLE 3

Storage Stability of Preparations According to DE-A-40 26 756 (Comparative Experiments)

Preparations according to Examples 7 (Table 4) and 8 (Table 5) in DE-A-40 26 756 were prepared by mixing the substances and stirring them for at least 3 hours at room temperature. The appearance of the preparations directly after they had been prepared and after storage for one day at −5° C. was observed. As can be seen from Tables 4 and 5, the preparations are insufficiently stable or insufficiently stable at low temperature.

TABLE 4

| Apr. 5, 1999 | A | B | C | D | E | F | G |
|---|---|---|---|---|---|---|---|
| Dehydracetic acid | 10.0 | 10.0 | | | | | 10.0 |
| Benzoic acid | 10.0 | 10.0 | 10.0 | | 12.5 | | 10.0 |
| Sorbic acid | | | 10.0 | 20.0 | 12.5 | 25.0 | |
| Polyhexamethylene biguanide | 1.0 | | | | | | |
| Demin. water | 4.0 | 5.0 | 5.0 | 5.0 | | | |
| Benzyl alcohol | 37.5 | 37.5 | 37.5 | 37.5 | 37.5 | 37.5 | 27.8 |
| Phenoxypropanols | 37.5 | 37.5 | 37.5 | 37.5 | 37.5 | 37.5 | 52.2 |

TABLE 4-continued

| Apr. 5, 1999 | A | B | C | D | E | F | G |
|---|---|---|---|---|---|---|---|
| Appearance Apr. 5, 1999 | clear, yellow solution | clear, yellow solution | white precipitate in colourless solution | white precipitate in colourless solution | white precipitate in colourless solution | white precipitate in colourless solution | clear, yellow solution |
| Precipitate volume relative to the total amount | | | ca. 10% | ca. 25% | ca. 15% | ca. 40% | |
| Samples A, B and G were stored at −5° C. on Apr. 5, 1999 | | | | | | | |
| Appearance of −5° C. sample on May 5, 1999 | yellow precipitate in yellow solution | yellow precipitate in yellow solution | | | | | yellow precipitate in yellow solution |
| Precipitate volume relative to the total amount | ca. 25% | ca. 25% | | | | | ca. 60% |

TABLE 5

| Apr. 5, 1999 | A | B | C | D | E | F | G |
|---|---|---|---|---|---|---|---|
| Dehydracetic acid | 10.0 | 10.0 | | | | | 10.0 |
| Benzoic acid | 10.0 | 10.0 | 10.0 | | 14.0 | | 10.0 |
| Sorbic acid | | | 10.0 | 20.0 | 14.0 | 28.0 | |
| Polyhexamethylene biguanide | 2.0 | | | | | | |
| Demin. water | 6.0 | 8.0 | 8.0 | 8.0 | | | |
| Benzyl alcohol | 25.0 | 25.0 | 25.0 | 25.0 | 25.0 | 25.0 | 27.8 |
| Phenoxyethanol | 47.0 | 47.0 | 47.0 | 47.0 | 47.0 | 47.0 | 52.2 |
| Appearance Apr. 5, 1999 | cloudy, yellow solution | clear, yellow solution | white precipitate in colourless solution | white precipitate in colourless solution | white precipitate in colourless solution | white precipitate in colourless solution | clear, yellow solution |
| Precipitate volume relative to the total amount | | | ca. 15% | ca. 30% | ca. 20% | ca. 40% | |
| Samples A, B and G were stored at −5° C. on Apr. 5, 1999 | | | | | | | |
| Appearance of −5° C. sample on May 5, 1999 | yellow precipitate in yellow solution | yellow precipitate in yellow solution | | | | | yellow precipitate in yellow solution |
| Precipitate volume relative to the total amount | ca. 80% | ca. 95% | | | | | ca. 40% |

EXAMPLE 4

Method to Determine the Preserving Action of Chemical Preservatives in Cosmetic Formulations Principle Using the method described, it is possible to examine the effectiveness of chemical preservatives with regard to pack preservation for cosmetic formulations. To this end, the preservatives to be investigated are added in varying concentrations to the unpreserved samples in various experimental formulations. A continuous microbial burden is achieved by periodically inoculating the experimental formulations. At the same time as the inoculation, streaks of each of the individual formulations are made immediately beforehand. Assessment is made by reference to the microbial growth of the streaks. The longer the period before the first appearance of microbial growth, the more effective the preservative.

Solutions and Nutrient Media

CSA (casein peptone soya flour peptone agar)
SA (Sabouraud dextrose agar)
SA slant tube
CSA+TLSH (No. 4)
SA-TLSH (No. 10)
NaCl (physiological sodium chloride solution, 8.5%)

Test Microbes

| Group 1 (Koko 1) | Staphylococcus aureus | ATCC 6538 |
|---|---|---|
| | Staphylococcus epidermis | ATCC 12228 |
| Group 2 (Koko 2) | Enterobacter gergoviae | Dr. Eigener/ Beiersdorf 1994 |
| | Escherichia coli | ATCC 11229 |
| | Klebsielle pneumoniae | ATCC 4352 |
| Group 3 (Koko 3) | Pseudomonas aeruginosa | ATCC 15442 |
| | Pseudomonas fluorescens | ATCC 17397 |
| | Pseudomonas putida | ATCC 12633 |
| Group 4 (Koko 4) | Aspergillus niger | ATCC 6275 |
| | Penicillium funiculosum | ATCC 36839 |
| | Candida albicans | ATCC 10231 |
| Group 5 (mixed suspension) | the microbes of all four groups | |

Cultivation of the Test Microbes

Bacteria: streaking with a sterile glass rod on CS agar
Yeasts: streaking using a sterile glass rod on SA agar
Fungi: *Aspergillus niger* is transferred to 4 Sa slant tubes

*Penicillium funiculosom* is transferred to Sa agar plates

All test microbes are incubated at 25° C.±2° C. for one week.

The test microbes are replaced at intervals of from 3 to 4 months.

Preparation of the Inoculation Solution (Groups 1 to 3)

The bacteria are rinsed off with 5 ml of NaCl in each case, filtered through a glass funnel containing glass wool into a 100 ml measuring cylinder and made up to 100 ml with NaCl. The bacterial suspensions have a titer of ca. $10^9$ CFU/ml.

Preparation of the Inoculation Solution (Group 4)

Three *Aspergillus niger* slant tubes are each shaken with 3 ml of NaCl on a Heldolph stirrer and introduced through a glass funnel containing glass wool. The yeast *Candica albicans* is rinsed off with 5 ml of NaCl and likewise poured through the glass funnel. 5 ml of a *Penicillium funiculosum* suspension (for the preparation of the fungal suspension see test instruction No. 22) are added to this mixture and made up to 100 ml with NaCl. The fungal suspension has a titer of ca. $10^5$ to $10^9$ CFU/ml.

Preparation of the Inoculation Solution (Group 5)

The inoculation solution is prepared as described above (Groups 1 to 4). After rinsing off, these are mixed and only then made up to 100 ml with NaCl.

All of the microbial suspensions are introduced separately into sterile glass-stoppered bottles containing glass beads and shaken for 5 min at a shaking frequency (to and fro movement) of 200 units/min. The microbial content of the mixed suspension is $10^9$ CFU/ml. The suspensions should be used on the day of preparation, but can also be used after storage in a refrigerator after 24 hours.

Implementation

In separate formulations, the preservatives to be investigated are added in varying concentrations to 25 g of the cosmetic to be tested in each case. The growth control used in each case is an unpreserved product sample. The test formulations are streaked onto CSA/TLSH and Sa/TLSH once per week following thorough stirring with a sterile glass rod, the first streaking being carried out directly prior to reinoculation. All samples are inoculated with 0.1 ml of the respective microbial suspension and thoroughly stirred.

The microbial growth of the streaks is assessed after incubation for three days at 25° C.±2° C. To be on the safe side, negative streaks are observed for a further 2 days and reassessed. The preservative action of the individual product concentrations is assessed in a semiqualitative method by means of the growth of the 5 individual streaks.

The test is usually carried out over six inoculation cycles and terminated after massive growth on two occasions.

Assessment of the Results

A preservative is considered good if it exists under the laboratory conditions given above for a period of 6 weeks without microbial attack of the sample formulations, i.e. even after the sixth inoculation, no microbial growth can be detected.

EXAMPLE 5

Improvement in the Colour Stability of the Liquid Concentrates According to the Invention EXAMPLE 5a The liquid concentrates A and B below were mixed:

|  |  | A | B |
|---|---|---|---|
| K sorbate | [% by wt.] | 15 | 15 |
| Na benzoate | [% by wt.] | 30 |  |

-continued

|  |  | A | B |
|---|---|---|---|
| K benzoate | [% by wt.] |  | 30 |
| Phenoxyethanol | [% by wt.] | 5 | 5 |
| Demin. $H_2O$ | [% by wt.] | 50 | 50 |
| Hazen colour number | zero value | 66 | 75 |
|  | 1 month 25° C. | 121 | 110 |
|  | 1 month 40° C. | 397 | 314 |

Result:

Replacing Na benzoate for K benzoate improves the colour stability of the preparation, which is shown in particular in the example of storage at 40° C., which is a measure of long-term stability.

EXAMPLE 5b

30% by weight of Na benzoate, 15% by weight of K sorbate, 5% by weight of phenoxyethanol and 50% by weight of demineralized water were stirred together to give a liquid concentrate. Filtration over a fluted filter gave a clear solution (Hazen colour number 29). Storage in clear glass at 25° C. and 40° C. gave clear, yellowish solutions. After storage (8 weeks) at 25° C. and 40° C., the Hazen colour number was 186 and 437 respectively.

EXAMPLE 5c 22.87% by weight of benzoic acid, 23.36% by weight of 45% strength potassium hydroxide solution, 15% by weight of K sorbate, 5% by weight of phenoxyethanol and 33.37% by weight of demineralized water (demin. $H_2O$) were stirred together; this concentrate has a K benzoate content of 30% by weight. Filtration over a fluted filter gave a clear solution with a Hazen colour number of 54. The liquid concentrates were stored in clear glass at 25 and 40° C. Following storage over 8 weeks at 25° C. and 40° C. the Hazen colour number was determined as 105 and 279 respectively.

EXAMPLE 5d

Colour Stabilization Using Sodium Citrate

A liquid concentrate comprising 18.75% by weight of K sorbate, 31.25% by weight of phenoxyethanol, 31.25% by weight of benzyl alcohol and 18.75% by weight of demineralized water was formulated, giving a clear, yellow solution having a Hazen colour number of 84. After storage for 6 months at room temperature the solution is still clear yellow and has a Hazen colour number of 229. However, if 0.1 part of sodium citrate is added to 100 parts of the freshly prepared solution, then the Hazen colour number changes from 87 (zero value) to 200 (after storage for 6 months at room temperature).

EXAMPLE 5e

A concentrate comprising 15.0% by weight of K sorbate, 5% by weight of phenoxyethanol, 30.0% by weight of sodium benzoate and 50% by weight of demineralized water was mixed, giving a clear, yellow solution with a Hazen colour number of 47. After storage for 6 months at room temperature the solution is still clear yellow and has a Hazen colour number of 233. However, if 0.1 or 0.05 part of sodium citrate is added to 100 parts of a freshly prepared solution of this composition, then the Hazen colour number changes from 49 or 52 respectively (zero value) to 114 or 132 respectively (after storage for 6 months at room temperature).

Result:

The addition of sodium citrate significantly improves the colour stability of liquid concentrates according to the invention.

EXAMPLE 5f

Effect of the Addition of DL-α-tocopherol or DL-α-tocopherol Acetate

A concentrate comprising 18.75% by weight of K sorbate, 31.25% by weight of benzyl alcohol, 31.25% by weight of phenoxyethanol and 18.75% by weight of demineralized water was mixed, giving a clear, slightly yellowish solution. Small amounts (parts by weight) of the antioxidant DL-α-tocopherol or DL-α-tocopherol acetate were added to 100 parts by weight of this freshly prepared solution. The Hazen colour numbers were determined immediately and after storage for 4 weeks at 50° C.:

|  | X | A | B | C | D | E | F |
|---|---|---|---|---|---|---|---|
| DL-α-tocopherol [pts.] | — | 0.005 | 0.01 | 0.02 | — | — | — |
| DL-α-tocopherol acetate (pts.) | — | — | — | — | 0.005 | 0.01 | 0.02 |
| Hazen colour number (zero value) | 62 | 60 | 58 | 58 | 54 | 54 | 56 |
| Hazen colour number (4 weeks at 50° C.) | 796 | 308 | 251 | 228 | 652 | 325 | 267 |

[pts.] = [parts by weight]

Result:

Both antioxidants significantly improve the colour stability.

EXAMPLE 6

Preparations Containing Various Cosmetics Additives

EXAMPLE 6a

To 100 parts by weight of a preparation consisting of 18.75% by weight of K sorbate, 31.25% by weight of phenoxyethanol, 31.25% by weight of benzyl alcohol and 18.75% by weight of demineralized water were added, in individual experiments, up to 4 parts by weight of a number of cosmetics additives, and the compatibility was tested (test for absence of precipitates and/or severe discolorations). The following additives have proven to be sufficiently compatible: dexpanthenol (care additive), farnesol (deodorant active ingredient), ascorbic acid and sodium ascorbate, vitamin E, 3-tert-butyl-4-hydroxyanisole, 2,6-di-tert-butyl-p-cresol (antioxidants), Sensiva SC 50 (deodorant active ingredient), benzalkonium chloride, the potassium salt of mandelic acid, 3-phenyl-1-propanol, phenethyl alcohol, ethylparaben, Glydant XL 1000 (1,3-dimethylol-5,5-dimethylhydantoin, DMDMH), iodopropynylbutyl carbamate and benzisothiazolone (antimicrobial active ingredients). The abovementioned preparation was incompatible with the antimicrobial active ingredients Vantocil IB (polyhexamethylene biguanide), bronopol and dibromodicyanobutane since in each case the addition of these active ingredients and storage led to severe discoloration of the solution.

EXAMPLE 6b

To 100 parts by weight of a preparation consisting of 15% by weight of K sorbate, 30% by weight of Na benzoate, 5% by weight of phenoxyethanol and 50% by weight of demineralized water were added, in individual experiments, up to 4 parts by weight of a number of cosmetics additives, and the compatibility was tested (test for absence of precipitates and/or severe discolorations). The following additives have proven sufficiently compatible: dexpanthenol (care additive), farnesol (deodorant active ingredient), ascorbic acid and sodium ascorbate, vitamin E, 3-tert-butyl-4-hydroxyanisole, 2,6-di-tert-butyl-p-cresol (antioxidants), Sensiva SC 50 (deodorant active ingredient), benzalkonium chloride, the potassium salt of mandelic acid, 3-phenyl-1-propanol, phenethyl alcohol, ethylparaben, Glydant XL 1000 (DMDMH), iodopropynylbutyl carbamate and benzisothiazolone (antimicrobial active ingredients). The abovementioned preparation was incompatible with the antimicrobial active ingredients Vantocil IB (polyhexamethylene biguanide), bronopol and dibromodicyanobutane since in each case the addition of these active ingredients and storage led to severe discoloration of the solution.

EXAMPLE 6c

A preparation consisting of 18.75% by weight of K sorbate, 28.75% by weight of benzyl alcohol, 28.75% by weight of phenoxyethanol, 18.75% by weight of demineralized water and 5% by weight of cosmetics additive was prepared. The following additives were found, in independent experiments, to be sufficiently compatible: methylparaben (preservative), propylparaben (preservative), Sensiva SC 50 (skincare additive, deodorant active ingredient) and Dowicil 200 (chloroallyladamantane derivative, preservative).

EXAMPLE 7

Colour Stability of Liquid Concentrates Having Varying Contents of Phenoxyethanol Three different preparations containing varying amounts of phenoxyethanol were prepared:

|  |  | A | B | C |
|---|---|---|---|---|
| Na benzoate | [% by wt.] | 30 | 30 | 30 |
| K sorbate | [% by wt.] | 15 | 15 | 15 |

-continued

|  |  | A | B | C |
|---|---|---|---|---|
| Phenoxyethanol | [% by wt.] | 3 | 5 | 10 |
| Demin. H$_2$O | [% by wt.] | 52 | 50 | 45 |
| pH |  | 9.0 | 9.1 | 9.2 |
| Hazen colour number zero value |  | 123 | 131 | 133 |

Following filtration, the solutions are clear, yellowish and stable and are completely miscible with water.

EXAMPLE 8

Preparation Based on K Sorbate+Phenoxyethanol in Water 30.77 parts of K sorbate+38.46 parts of phenoxyethanol+ 30.77 parts of demin. water (demin.=demineralized). This gives a clear, yellow solution, Gardner colour number 2.5. (The Gardner colour number was determined in accordance with DIN 6161).

The invention claimed is:

1. A liquid concentrate for preserving cosmetics, comprising:
    a sorbic acid salt (A);
    an alcohol component (B) selected from the group consisting of phenoxyethanol, benzyl alcohol, and mixtures thereof; and
    water as a solvent (C),
    the total content of components A and B being greater than 80% by weight, wherein said concentrate has a pH above 7, and wherein said liquid concentrate does not contain polyhexamethylene biguanide salts, wherein said concentrate comprises 18.75% by weight of K sorbate, 31.25% by weight of 2-phenoxyethanol, 31.25% by weight of benzyl alcohol and 18.75% by weight of water.

2. The liquid concentrate according to claim 1, further comprising auxiliaries, additives and/or active ingredients selected from the group consisting of citric acid and salts thereof, mandelic acid and salts thereof, dimethyldimethylolhydantoin, 2,6-di-tert-butyl-p-cresol, 3-tert-butyl-4-hydroxyanisole, 1-(2-ethylhexyl)-glyceryl ether or 3-((2-ethylhexyl)oxy)-1,2-propanediol), ascorbic acid or salts thereof, 6-0-palmitoyl-L-ascorbic acid, vitamin E and gallic acid.

3. The liquid concentrate according to claim 2, further comprising alkali metal citrates, alkali metal mandelates or vitamin E.

4. The liquid concentrate according to claim 1, wherein the sorbic acid salt is K sorbate.

5. A method for the preservation of cosmetic products, comprising adding to said cosmetic product an efficient amount of a liquid concentrate according to claim 1.

6. The method according to claim 5, wherein the cosmetic products are "rinse-off" products.

7. The method according to claim 6, wherein the "rinse-off" products are shampoos.

8. A method for the preservation of cosmetic products, consisting of adding to said cosmetic product an efficient amount of a liquid concentrate according to claim 1.

9. A liquid concentrate for preserving cosmetics, comprising:
    a sorbic acid salt (A);
    an alcohol component (B) selected from the group consisting of phenoxyethanol, benzyl alcohol, and mixtures thereof;
    water as a solvent (C); and
    a color stabilizing agent (D) in an amount sufficient to stabilize the color of the liquid concentrate, said color stabilizing agent comprising an alkali metal citrates or alkali metal mandelate, and
    wherein the total content of components A and B being greater than 45% by weight, wherein said concentrate has a pH above 7, and wherein said liquid concentrate does not contain polyhexamethylene biguanide salts, wherein said concentrate comprises 18.75% by weight of K sorbate, 31.25% by weight of 2-phenoxyethanol, 31.25% by weight of benzyl alcohol and 18.75% by weight of water.

10. The liquid concentrate according to claim 9, further comprising auxiliaries, additives and/or active ingredients selected from the group consisting of dimethyldimethylolhydantoin, 2,6-di-tert-butyl-p-cresol, 3-tert-butyl-4-hydroxyanisole, 1-(2-ethylhexyl)-glyceryl ether or 3-((2-ethyl-hexyl)oxy)-1,2-propanediol), ascorbic acid or salts thereof, 6-0-palmitoyl-L-ascorbic acid, vitamin E and gallic acid.

11. The liquid concentrate according to claim 10, further comprising vitamin E.

12. The liquid concentrate according to claim 9, wherein the total content of components A and B is greater than 80% by weight.

13. The liquid concentrate according to claim 9, wherein the sorbic acid salt is K sorbate.

14. The liquid concentrate according to claim 9, wherein the color stabilizing agent is sodium citrate.

15. A method for the preservation of cosmetic products, comprising adding to said cosmetic product an efficient amount of a liquid concentrate according to claim 9.

* * * * *